United States Patent [19]

Burns

[11] Patent Number: 5,445,619
[45] Date of Patent: Aug. 29, 1995

[54] SHIELDED NEEDLE ASSEMBLY

[75] Inventor: James A. Burns, Elizabeth, N.J.

[73] Assignee: Becton, Dickinson and Company, Franklin Lakes, N.J.

[21] Appl. No.: 311,695

[22] Filed: Sep. 23, 1994

[51] Int. Cl.⁶ .............................................. A61M 5/32
[52] U.S. Cl. ................... 604/192; 604/263; 128/919
[58] Field of Search ................ 604/192, 187, 263; 128/919

[56] References Cited

U.S. PATENT DOCUMENTS

| | | | |
|---|---|---|---|
| 4,966,591 | 10/1990 | Yoen | 604/263 X |
| 4,976,699 | 12/1990 | Gold | 604/192 |
| 5,151,089 | 9/1992 | Kirk, III et al. | 604/263 X |
| 5,207,653 | 5/1993 | Janjua et al. | 604/192 |
| 5,312,369 | 5/1994 | Arcusin et al. | 604/192 |

*Primary Examiner*—John D. Yasko
*Attorney, Agent, or Firm*—Arthur D. Dawson

[57] ABSTRACT

A shielded needle assembly includes an elongate needle having a pointed distal end, a proximal end and a passageway therethrough. The assembly further includes a hub having an opening for receiving the needle so that said distal end of said needle projects outwardly, and has elements for releasably mounting the hub on a fluid handling device. The assembly has a shield having an open end, a closed end, a sidewall having a slot extending from the open end toward the closed end, and an arm extending radially outwardly at the open end opposite the slot. The shield has a first position at which the needle is exposed for use and a second position at which the shield substantially obstructs access to the needle. The slot provides clearance for the needle. A mounting rotatably holds the shield onto the hub. The mounting has a first pivot for pivotally attaching the shield to the mounting at the arm. The mounting further includes a second pivot having activating elements pivotally attached for interacting with the arm so that movement of the activating elements about the second pivot by the user causes movement of the shield from the first position toward the second position.

20 Claims, 6 Drawing Sheets

SHIELDED NEEDLE ASSEMBLY

BACKGROUND OF THE INVENTION

1. Field of the Invention

The present invention relates to a safety shield for a needle and more particularly to a safety shield assembly which attaches to the hub of the needle, and allows use of the needle on a syringe, needle holder or other fluid handling device.

2. Description of Related Information

In the medical arts, sharp pointed needles are used for a variety of procedures. Devices having sharp pointed needles are used for administering fluids to patients either directly or into intravenous apparatus, and in various blood drawing applications either with syringes or with specialized holders for filling evacuated tubes.

Exposure to blood borne pathogens is a recognized hazard by anyone associated with the medical arts. As a result of this recognition, numerous protocols for use of needles have been developed and are practiced. The problem of transmission of blood borne pathogens not only exists for the physician, nurse or phlebotomist using the needles, but also for support workers all through the hospital. Since most needles in use today are single-use and disposable, hospital service personnel are at risk from needles that are not properly handled by the users.

The use protocols generally dictate in detail when and how a needle will be used and how it should be disposed of. The problem with many protocols for handling needles is that they often require users to perform additional steps in a procedure. With the press of time and simple carelessness certain practices regarding handling of used needles are sometimes disregarded and injuries still occur. The medical device industry has responded to the problem by producing a wide variety of sharps collectors, needle shielding devices and the like to assist practitioners in their need to reduce the occurrence of needle injuries.

Many devices have been developed for shielding needles after use to avoid exposing other workers to used needles. A representative listing of many of these devices is found in U.S. Pat. No. 4,982,842 to Hollister et al. Hollister et al. lists 90 U.S. patents of various devices for guarding a needle as part of the background for the present shielded needle container. Hollister et al. discloses a stand alone adapter that has male and female ends for mating with a needle assembly and the ejection end of a syringe. The device of Hollister et al. includes a housing mounted to the adapter which may be pivoted to a position in alignment with the needle for enveloping the needle and locking the needle to retain it in the housing. The Hollister et al. device increases the unusable or "dead" volume of the device on which the adapter is mounted, requires an additional part which increases the projection of the needle hub, and the mechanism for holding the cap onto the needle snaps onto the needle itself, which may create an aerosol of any fluid remaining on the needle. Also, if bevel position is important to the intended use of the needle, the Hollister et al. invention must be carefully aligned with the needle point when mounted.

U.S. Pat. 5,207,653 to Janjua et al. discloses a needle cap with a longitudinal slit having a width greater than the width of a needle. According to Janjua et al., the needle cap is adapted to be pivotally connected with the needle and hub piece. Janjua et al. also discloses that the needle cap is usable with a syringe or with a needle holder for fluid collection robes. The device disclosed by Janjua et al. mounts on the needle hub with a pivot, but since it only pivots in one plane, unless the needle point is precisely oriented with the hub during assembly, the shield may interfere in some applications.

Many of the devices listed in the background of the Hollister et al. patent, the Hollister et al. invention itself and the Janjua et al. invention all attempt to address the recognized need to protect medical and service personnel from needle sticks. There are several recurrent problems in varying degrees with all these devices. Many of the devices are somewhat complex, hence are significantly more costly than an unprotected device. Many of the devices increase the complexity or increase the difficulty of performing a procedure. Some devices are so specific that they preclude use of the device in certain procedures. For these and similar reasons most of the devices in the Hollister et al. background have never been successfully commercialized.

Blood drawing is one application that is particularly sensitive to needle point orientation. Most phlebotomists carefully align a needle point with the beveled face away from the skin so that the needle point placement may be precisely controlled. A needle assembly as disclosed in Janjua et al. would either sometimes be clumsy to use because the shield would sometimes be in the way or, alternatively, more expensive because of the need to carefully orient the point during assembly of the components in manufacture. Additionally, in Janjua et al., while there is a recognition of the need to secure the cap in the closed position over the needle, all of the solutions proposed require additional steps such as securing the cap with an adhesive or twisting the cap.

Although there already are many shielded needle devices, there is still a need for a shielded needle device that is easily manufactured, applicable to many devices and simple to use. Additionally, the needle device should not interfere with normal practices of use. Such a device is described below.

SUMMARY OF THE INVENTION

A shielded needle assembly includes an elongate needle having a pointed distal end, a proximal end and a passageway therethrough. The assembly includes a hub having a proximal end, a distal end and an outside surface. The hub has an opening therethrough for receiving the needle so that the distal end of the needle projects outwardly. The hub further includes elements for releasably mounting the hub on a fluid handling device. The preferred assembly includes a shield with an open end, a closed end and a sidewall with a slot extending from the open end toward the closed end. The shield includes an arm extending radially outwardly at the open end opposite the slot. The shield has a first position at which the needle is exposed for use and a second position at which the shield substantially obstructs access to the needle. The slot is sufficient to provide clearance for the needle. A mounting rotatably holds the shield onto the hub. The mounting includes a first pivot for pivotally attaching the shield to the mounting at the arm. The preferred mounting further includes a second pivot for pivotally attaching activating elements for interacting with the arm so that movement of the activating elements about the second pivot causes movement of the shield from the first position toward the second position. Preferably, the activating elements include a trigger positioned so that a user may cause movement of the trigger with a finger and move the shield from the first position to the second position. The shield thus locks in the second position.

In the preferred embodiment the needle projects proximally outwardly from the hub and includes a proximal point for penetrating a stopper of a fluid collection device. In this embodiment, the elements for releasably mounting the hub preferably include a proximal thread for mounting the hub on a needle holder.

In another embodiment, the elements for releasably mounting the hub on a fluid handling device include a proximal female luer fitting which may be mounted on a syringe or other fluid handling device having a male luer fitting.

In all of the embodiments of the assembly, mounting of the shield on the hub allows the shield to be rotated about the hub, thus no requirement is imposed on the manufacturing process for the assembly to orient the point. Additionally, the rotation of the mounting on the hub allows the safety needle assembly of the invention to be used on most standard fluid handling devices. The needle shield can easily be rotated out of the way when the needle is in use, and the trigger enables the shield to be readily moved to the second position to shield the needle without the user changing grip on the fluid handling device.

DETAILED DESCRIPTION

While this invention is satisfied by embodiments in many different forms, there is shown in the drawings and will herein be described in detail, several embodiments of the invention with the understanding that the present disclosure is to be considered as exemplary of the principles of the present invention and is not intended to limit the scope of the invention to the embodiments illustrated. The scope of the invention will be measured by the appended claims and their equivalents.

A convention adopted for this description is that the term "distal" refers to the direction away from a user of the invention and the term "proximal" refers to the direction toward the user.

Referring to FIGS. 1 to 5, a preferred shield needle assembly 10 of the present invention includes an elongate needle 12 having a longitudinal axis X, a pointed distal end 14, a proximal end 16 and a passageway 18 therethrough. The assembly includes a hub 20 with a proximal end 22, a distal end 24, an outside surface 26 having a diameter "a" and an opening 28 therethrough for receiving needle 12 so that distal end 14 projects outwardly. Hub 20 preferably has a circumferential groove 30 in outside surface 26 intermediate to the proximal and the distal end with an outside diameter "b" that is less than hub outside surface diameter "a". Hub 20 preferably includes provisions for releasably mounting the hub on a fluid handling device. In the preferred embodiment where the fluid handling device is a needle holder 34, preferably hub 20 includes male threads 36 on proximal end 22 are for mounting the hub on needle holder 34.

Needle assembly 10 preferably includes shield 38 having an open end 40, a closed end 42 and a sidewall 44 having an open slot 46 extending from open end 40 toward closed end 42. Shield 38 also includes an arm 48 extending radially outwardly at open end 40 opposite slot 46.

The preferred assembly includes a mounting 50 for rotatably holding shield 38 onto hub 20. Mounting 50 preferably includes a bushing 47 with an opening 51 therethrough having a sidewall 53. Sidewall 53 preferably has an inward projection 55 to mate with groove 30. Mounting 50 preferably includes a first pivot 49 for pivotally attaching the shield to the mounting at arm 48. Mounting 50 preferably further includes a second pivot 52 and a trigger 54 pivotally attached to second pivot 52 for interacting with arm 48 so that movement of the trigger about the second pivot causes movement of the shield from the first position toward the second position. Arm 48 preferably includes a first gear 56 with a radius "c" rotatably attached at first pivot 49 so that movement of the first gear moves shield 38 from the first position toward the second position. Trigger 54 includes a second gear 58 having a radius "d" meshing with first gear 56 so that movement of trigger 54 causes movement of shield 38 from the first position toward the second position. In an embodiment where second gear radius "d" is greater than first gear radius "c", movement of the trigger about second pivot causes proportionally greater movement of the shield from the first position toward the second position.

In a preferred embodiment of assembly 10, trigger 54 is positioned so that a user may move it with a finger. The preferred embodiment further includes radius "d" being about two times radius "c", with the shield first position being about 90 degrees from the shield second position about the first pivot. Thus, movement of trigger 54 with the user's finger through an arc of about 45 degrees about the second pivot causes shield 38 to move from the first position to the second position. In the preferred embodiment, first gear 56 and second gear 58 lock shield 38 in the second position. Preferably first gear 56 includes a tooth 64 for locking and second gear 58 includes a tooth 66 for locking. The locking teeth preferably are positioned so that locking tooth 64 and locking tooth 66 are in locking mesh when shield 38 is in the second position.

Preferably, locking tooth 64 includes a notch 68 and locking tooth 66 includes an enlarged contact surface 70 for engaging notch 68 when tooth 64 and tooth 66 are in locking mesh, thereby substantially preventing further movement of shield 38.

Assembly 10 preferably includes proximal end 16 of needle 12 projecting proximally from hub 20 and includes a proximal point 72 useful, for example, in penetrating a resilient stopper on a fluid collection tube and the like. One skilled in the art of medical devices will recognize that needle 12 may be formed as a single article having a proximal point on a proximal portion projecting proximally and a distal point on a distal portion projecting distally. Alternately, needle 12 may be two separate pieces, a distal piece projecting distally having a distal point and a proximal piece projecting proximally having a proximal point, with the pieces connected in fluid communication in the hub opening.

Figure 3:
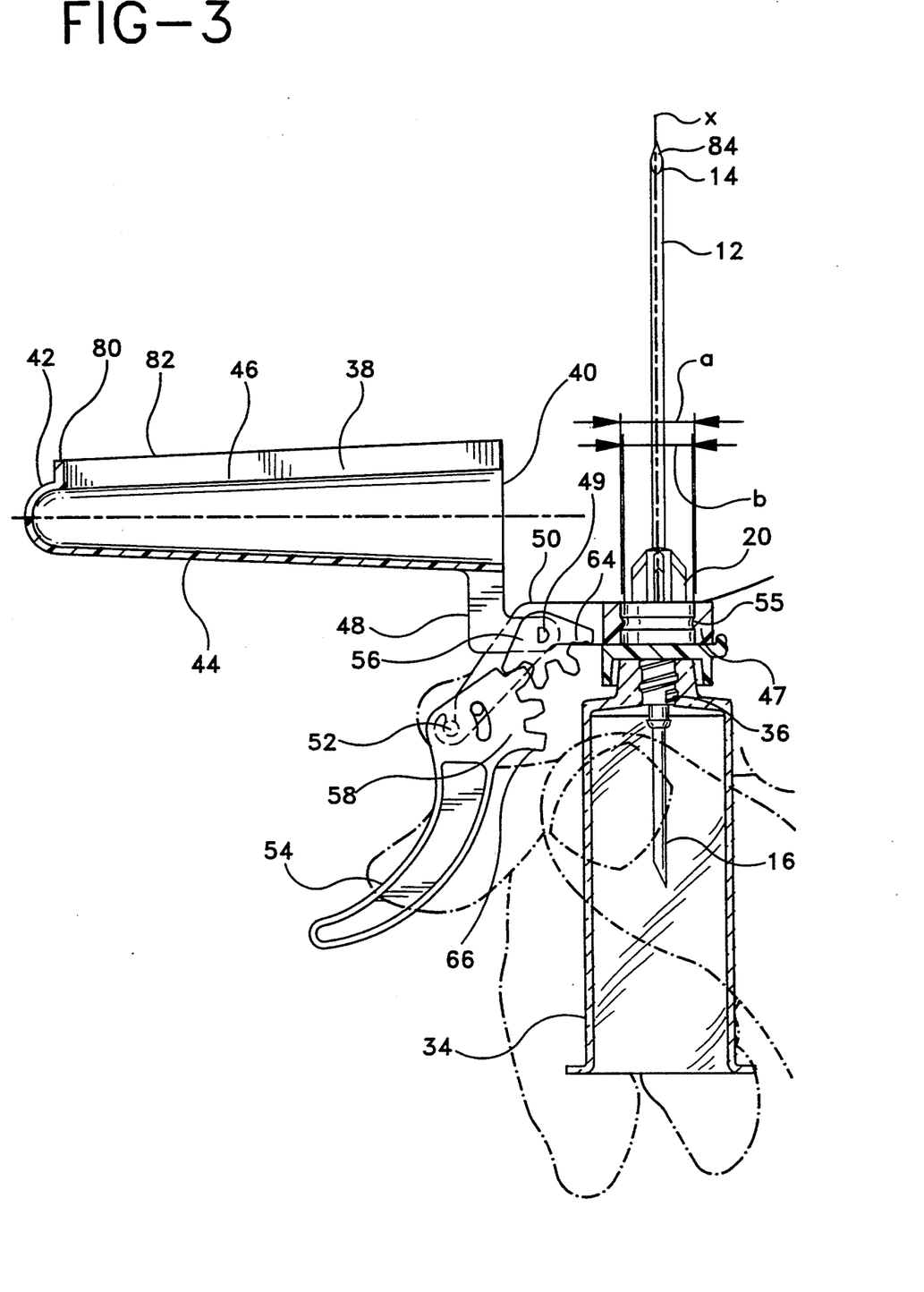
FIG. 3 is a schematic cross sectional view of the embodiment of FIG. 1 mounted on a needle holder with the shield in the first position, with a user's hand shown in phantom.
Figure 4:
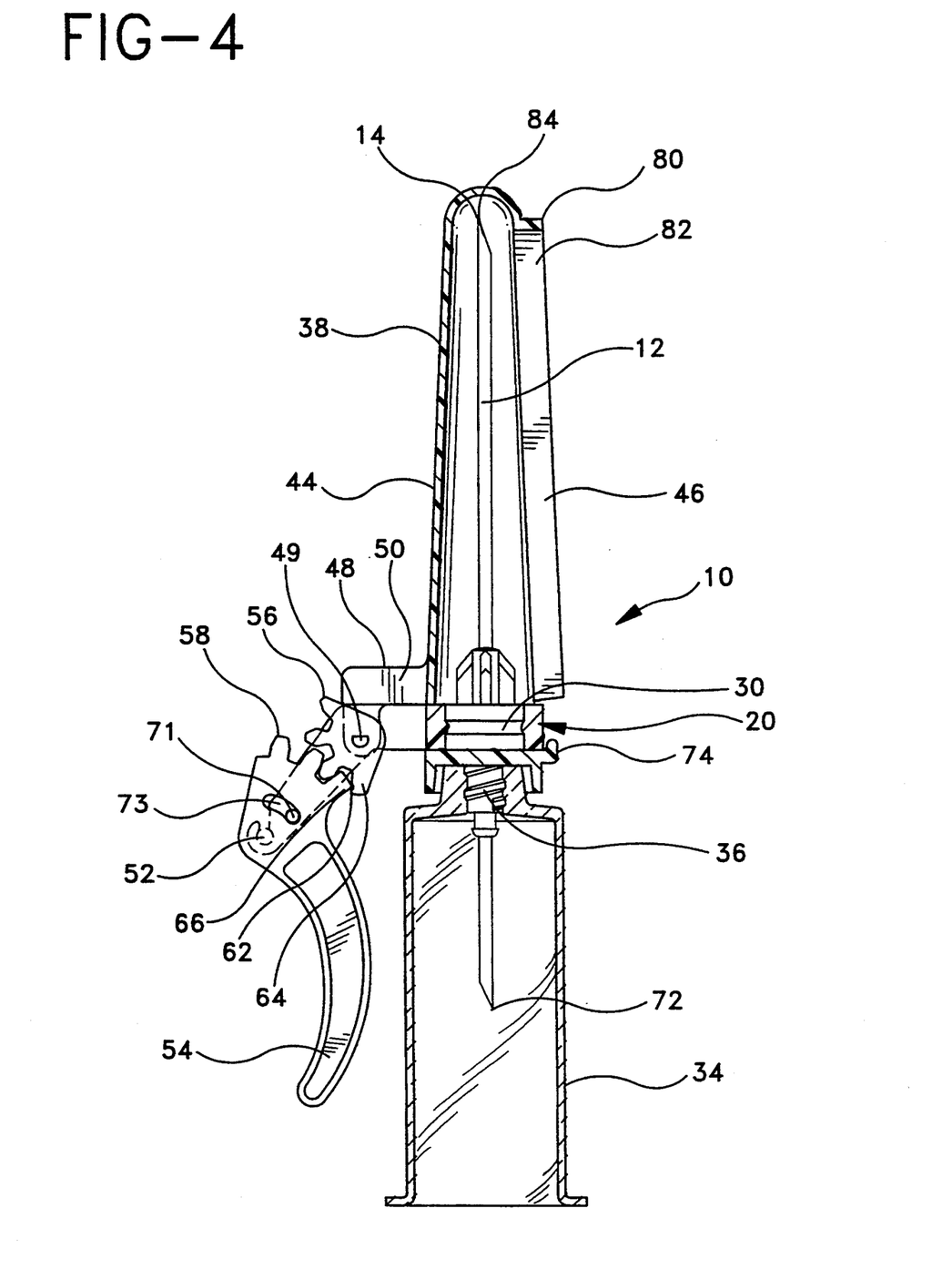
FIG. 4 is a schematic cross sectional view of the embodiment of FIG. 3 with the shield in the second position, without the user's hand.

As illustrated in FIG. 3, the preferred assembly is mounted on needle holder 34 and held in a user's hand. Shield 38 has a first position at which needle 12 is exposed. FIG. 4 illustrates shield 38 in a second position where shield 38 substantially obstructs unintentional access to needle 12. Slot 46 preferably provides sufficient clearance for needle 12 when shield 38 moves from the first position to the second position. Preferably, mounting 50 further includes a protrusion 71 adjacent second pivot 52 sized to fit within an aperture 73 fin second gear 58 serving in a cam/cam follower relationship. Protrusion 71 serves to limit the range of motion of the trigger so that first gear 56 and second gear 58 remain in mesh, thereby defining the first position of the shield. In the preferred embodiment, male threads 36 are used to mount the assembly on needle holder 34. Hub 20 further preferably includes an outward projection 74 located proximally to groove 30 on the hub outside surface. Projection 74 allows mounting 50 to rotate less than one complete revolution around hub 20, thus allowing shield 38 to be easily rotated so as not to interfere with a procedure, but also allowing assembly 10 to be dismounted by unscrewing from a needle holder for disposal. Hub proximal end 22 preferably includes facets 75 to facilitate removal of the assembly fluid handling device by engaging the opening of the needle disposal device.

Figure 1:
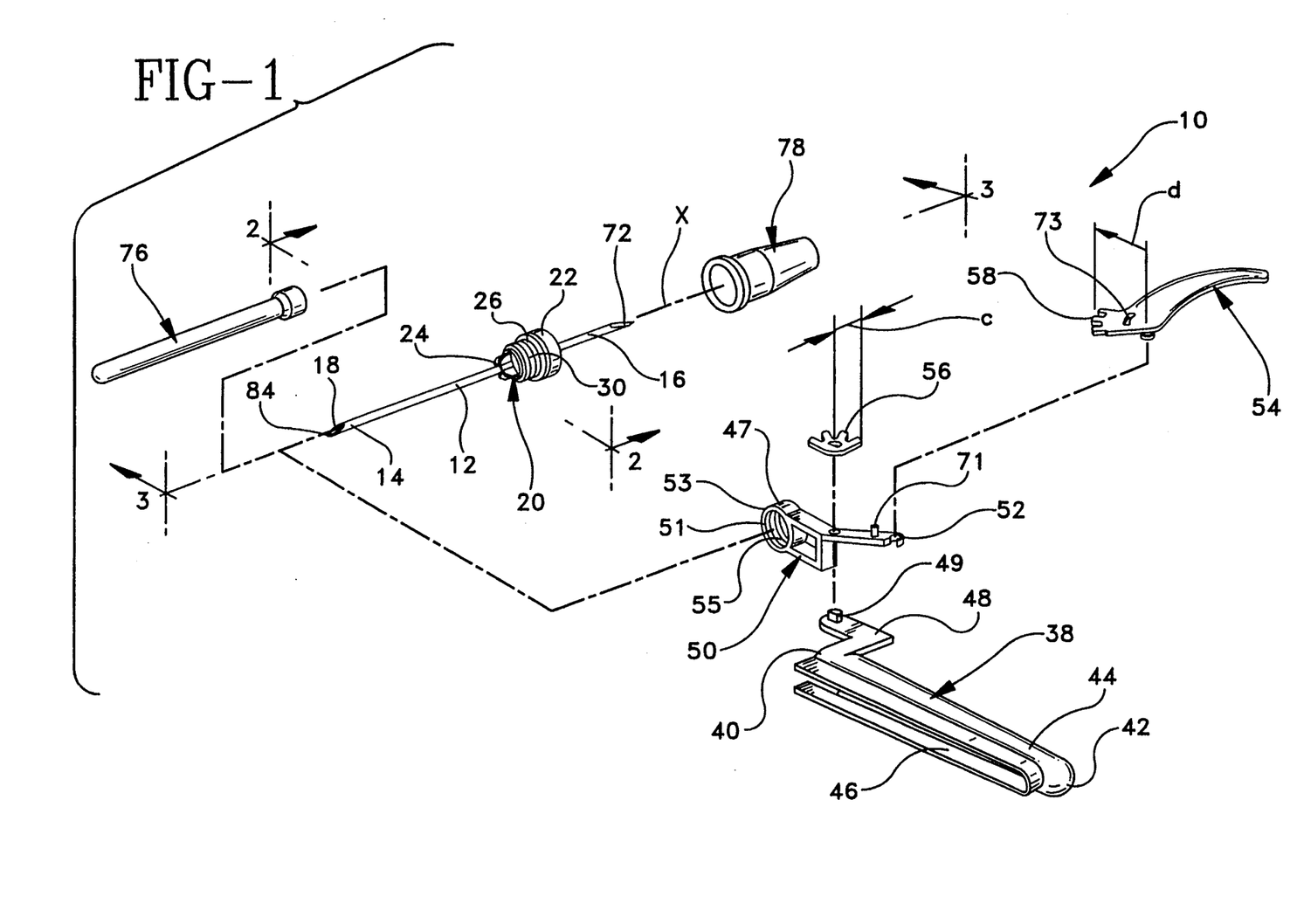
FIG. 1 is an exploded perspective view of a preferred embodiment of the present invention.
Figure 2:
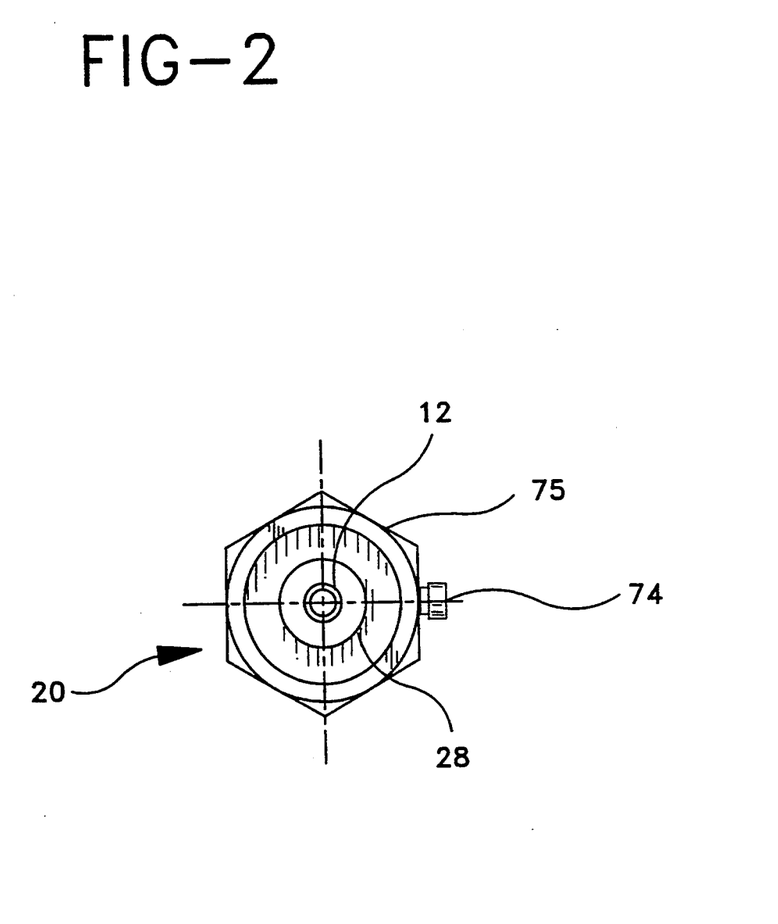
FIG. 2 is a sectional view along the line 2—2 of the hub portion of the embodiment of FIG. 1.

Assembly 10 preferably further includes a removable distal cover 76 releasably mounted on hub 20 for coveting needle 12 projecting distally from the hub and a removable proximal cover 78 for coveting proximal portion 16 of the needle. The covers 76 and 78 provide physical protection for the distal and proximal projections of the needle until the covers are removed.

In the manufacturing process for the preferred assembly, needle 12 preferably is fixedly mounted in hub 20 with an adhesive, a needle lubricant applied to the needle, then distal cover 76 and proximal cover 78 are mounted on hub 20 to protect the needle. Preferably distal cover 76 mounts on hub distal end 24 and has an outside diameter smaller than diameter "b", thereby allowing opening 51 to pass over the cover when mounting 50 is placed on hub 20 at groove 30.

Preferred shield 38 includes a perimeter 80 around slot 46. Preferably perimeter 80 includes a raised rib 82 to substantially reduce spatter from any fluid remaining on needle 12 when a procedure is completed. Preferably shield 38 and mounting 50 are formed from a thermoplastic resin. Suitable resins include but are not limited to polyethylene, polycarbonate, polystyrene, polypropylene, copolymers of polyethylene and polypropylene and the like. Polypropylene, polyethylene and copolymers of polypropylene are preferred.

In using the preferred assembly on a needle holder for performing phlebotomy, the ability to rotate shield 38 about hub 20 is a particular benefit. The technique practiced by phlebotomists generally requires that distal point 14 be aligned so that a face 84 of distal point 14 be aligned so that face 84 is up (away from the patient). This bevel placement allows phlebotomist to precisely position the needle point for the puncture. The precise position allows the phlebotomist to minimize the angle of entry of the needle into the vein. A minimum penetration angle reduces the incidence of penetration of the needle through the far wall of the vein. Most other shield devices are attached to the needle holder or to the hub with a fixed pivot and the like and cannot be rotated about the hub. Thus, with these devices, there is a requirement for careful orientation of the needle point to the hub during manufacture. The need for point orientation imposes an additional and critical requirement on the manufacturing process, adding an additional step, potentially slowing the rate of manufacture and possibly decreasing the yield. The present invention imposes no point orientation requirement thereby allowing the current manufacturing process to be retained.

Figure 5:
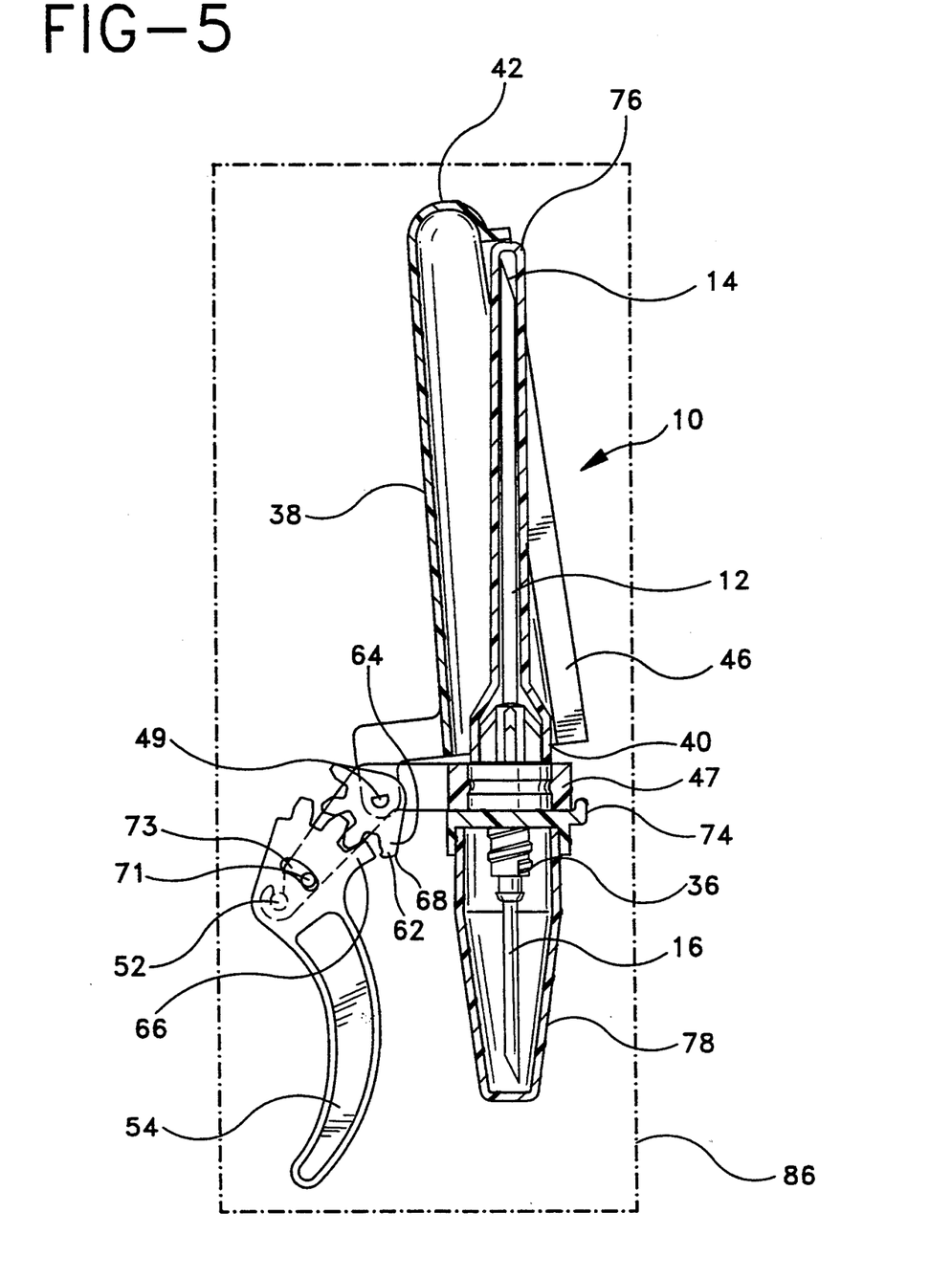
FIG. 5 is a schematic cross sectional view of the embodiment of FIG. 1 with the shield between the first and the second positions as it would be packaged for shipment to the user.

Referring to FIG. 5, assembly 10 may be configured so that shield 38 is intermediate to the first position and the second position and sealed in a package (schematically illustrated as reference number 86 in the drawings) formed from materials resistant to the passage of microorganisms and exposed to conditions that render microorganisms present in the package substantially non-viable. Generally, in the medical device industry, exposure of a packaged device to ethylene oxide or to ionizing radiation is used to render microorganisms non-viable and the device within the package is defined as sterile. The configuration of the shield in the intermediate position allows the assembly to require less package space than it would require in the first position, thus minimizing the space required in sterilization, shipping and storage. After the exposure, the packaged assembly is sterile until package 86 is opened. Additionally, covers 76 and 78 serve to keep needle 12 sterile until removed.

In preparation for normal usage of the preferred assembly for a blood drawing procedure, package 86 is opened, assembly 10 removed, then proximal cover 76 is removed, the assembly mounted onto needle holder 34 using threads 36 and shield 38 moved to the first position. Immediately prior to the use in the procedure, distal cover 78 is removed and the procedure is conducted as described above.

Figure 6:
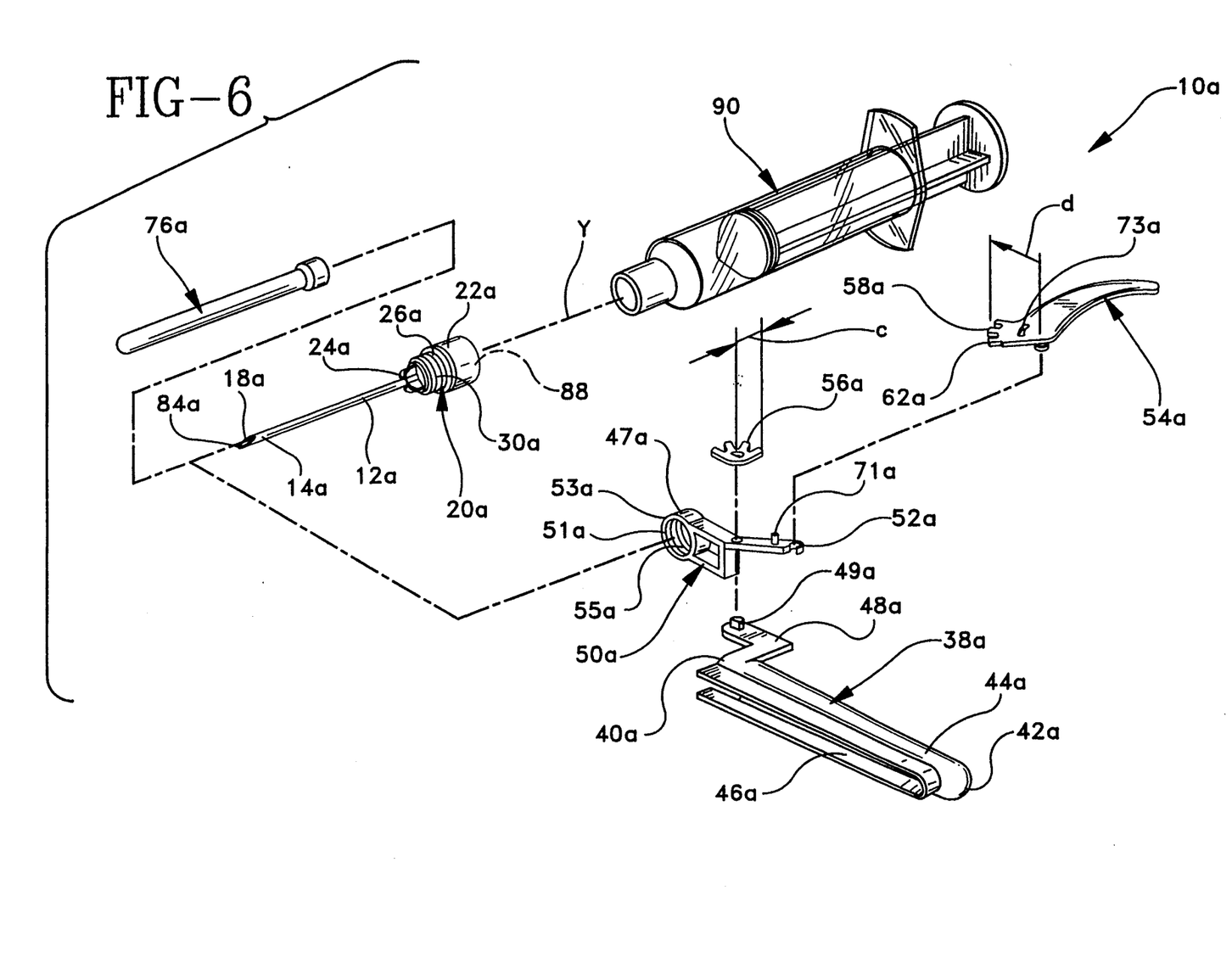
FIG. 6 is an exploded perspective view of an embodiment of the present invention mounted on a syringe with the shield in the first position.

FIG. 6 shows an alternate embodiment to the shielded assembly of FIGS. 1 through 5. In this embodiment there are elements similar in structure and function to the embodiment of the present invention shown in FIGS. 1 through 5. Accordingly, substantially similar components that perform substantially similar functions are numbered identically to those components of the embodiment of FIGS. 1 through 5 except that a suffix "a" is added to identify those components in FIG. 6.

As shown in FIG. 6 needle assembly 10a includes a needle 12a having a longitudinal axis y, a pointed distal end 14a, a proximal end 16a and a passageway 18a. In this embodiment a proximal female luer fitting 88 is used for mounting the hub on a syringe 90 or any other fluid handling device having a conjugate male luer fitting.

As is shown in the drawings, and described above, the needle assembly of the present invention allows the use of conventional fluid handling devices. The assembly permits most procedures to be performed in normal fashion with the important benefit of providing for shielding the needle without requiring any additional steps by the user other than an almost instinctive finger movement to move the shield from the first position to the second position.

What is claimed is:

1. A shielded needle assembly comprising:
   an elongate needle having a pointed distal end, a proximal end and a passageway therethrough;
   a hub having an axial opening therethrough for receiving said needle so that said distal end of said needle projects outwardly therefrom, said hub further including means for releasably mounting said hub on a fluid handling device;
   a shield having an open end, a closed end, a sidewall having a slot extending from said open end toward said closed end, and an arm extending radially outwardly at said open end opposite said slot, said shield having a first position at which said needle is exposed for use and having a second position at which said shield substantially obstructs access to said needle, said slot being sufficient to provide clearance for said needle;
   a mounting for rotatably holding said shield onto said hub, said mounting having a first pivot for pivotally attaching said shield to said mounting at said arm, said mounting including a second pivot; and
   activating means pivotally attached to said mounting at said second pivot for interacting with said arm so that movement of said activating means about said second pivot causes movement of said shield from said first position toward said second position.

2. The assembly of claim 1 wherein said hub has a substantially circumferential outside surface and includes a circumferential groove having a diameter less than a diameter of said hub outside surface 3. The assembly of claim 2 wherein said mounting for holding said shield onto said hub includes a bushing having an opening including a sidewall for receiving said hub, said sidewall having at least one inward projection to mate with said groove on said hub thereby holding said mounting onto said hub and allowing rotation of said shield about said hub.

4. The assembly of claim 1 further including a removable distal cover releasably mounted on said hub for covering and providing physical protection for said needle projecting distally until said distal cover is removed.

5. The assembly of claim 1 wherein said proximal end of said needle projects proximally outwardly from said hub and includes a point, and said means for releasably mounting said hub on said fluid handling device comprises a proximal external thread on said hub for mounting said hub on said fluid handling device.

6. The assembly of claim 5 wherein said hub outside surface further includes an outward projection located proximally to said groove, said projection preventing a complete rotation of said bushing about said hub thereby allowing said assembly to be removed from said fluid handling device into a needle collection device.

7. The assembly of claim 6 wherein said hub outside surface has a faceted proximal portion for engaging said hub with the needle collection device.

8. The assembly of claim 5 further including a removable proximal cover releasably mounted on said hub for covering said needle projecting proximally from said hub and a removable distal cover releasably mounted on said hub for coveting said needle projecting distally from said hub, said proximal cover and said distal cover providing physical protection for said needle projecting proximally and distally, respectively, until said covers are removed.

9. The assembly of claim 1 wherein said means for releasably mounting said hub on said fluid handling device comprises a proximal female luer fitting.

10. The assembly of claim 1 wherein said slot has a perimeter comprising a raised rib.

11. The assembly of claim 1 wherein said shield and said mounting are formed from a thermoplastic resin selected from the group consisting of polyethylene, polypropylene and copolymers of polypropylene and polyethylene.

12. The assembly of claim 1 wherein said assembly is individually packaged in a package substantially providing a barrier to the passage of microorganisms until opened, said packaged assembly having been exposed to conditions to render any microorganisms in said package substantially nonviable.

13. The assembly of claim 1 wherein said arm further includes a first gear rotatably attached at said first pivot so that movement of said first gear thereby moves said shield from said first position toward said second position, said activating means including a second gear meshing with said first gear so that movement of said activating means causes movement of said shield from said first position toward said second position.

14. The assembly of claim 13 wherein said first gear has a first radius and said second gear has a second radius, said second radius being larger than said first radius so that movement of said activating means about said second pivot causes proportionally greater movement of said arm on said shield about said first pivot thereby causing proportionally greater movement of said shield from said first position toward said second position.

15. The assembly of claim 14 wherein said radius of said second gear is about two times the radius of said first gear, and said first position of said shield is about ninety degrees from said second position with respect to said first pivot so that moving said activating means through an arc of about forty five degrees about said second pivot thereby moves said shield from said first position to said second position.

16. The assembly of claim 15 wherein said first gear and said second gear further comprise means for locking said shield in said second position.

17. The assembly of claim 16 wherein said means for locking said shield in said second position includes said first gear having a tooth for locking and said second gear having a tooth for locking, said teeth being positioned so that said teeth are in locking mesh when said shield is in said second position thereby locking said shield in said second position.

18. The assembly of claim 17 wherein said first gear locking tooth includes a notch and said second gear locking tooth includes an enlarged contact surface for engaging said notch in said first gear locking tooth and substantially preventing further movement said first gear relative to said second gear, when said teeth are in said locking mesh.

19. The assembly of claim 1 wherein said activating means comprises a trigger positioned so that a user may cause movement of said trigger with a finger.

20. A shielded needle assembly comprising:
   an elongate needle having a pointed distal end, a proximal end and a passageway therethrough;
   a hub having a proximal end, a distal end and an outside surface having an outside diameter, said hub having an opening therethrough for receiving said needle so that said distal end of said needle projects outwardly therefrom, said hub further including a circumferential groove in said hub outside surface having an outside diameter less than said outside surface outside diameter and an outward projection on said outside surface located proximally to said groove, said hub further including means for releasably mounting said hub on a fluid handling device;

a shield having an open end, a closed end, a sidewall having a slot extending from said open end toward said closed end, said shield including an arm extending outwardly at said open end opposite said slot, said shield having a first position at which said needle is exposed for use and a second position at which said shield substantially obstructs access to said needle, said slot providing clearance for said needle; and a mounting for rotatably holding said shield onto said hub including a bushing having an opening with a sidewall, said opening for receiving said hub at said groove, said sidewall including at least one inward projection to mate with said groove for holding said shield on said hub and allowing rotation of said mounting about said hub, said mounting having a first pivot for pivotally attaching said arm, said arm further including a first gear fixedly attached to said arm at said first pivot so that a movement of said gear thereby moves said shield from said first position toward said second position, said mounting having a second pivot for pivotally attaching activating means for moving said shield, said activating means including a second gear positioned to mesh with said first gear so that, when said activating means is moved about said second pivot, said second gear meshes with said first gear causing said shield to move from said first position toward said second position, said first gear and said second gear further including means for locking said shield in said second position.

* * * * *